United States Patent
Tachibana et al.

(10) Patent No.: US 8,222,601 B2
(45) Date of Patent: *Jul. 17, 2012

(54) SCANNING ELECTRON MICROSCOPE AND METHOD OF IMAGING AN OBJECT BY USING THE SCANNING ELECTRON MICROSCOPE

(75) Inventors: Ichiro Tachibana, Hitachinaka (JP); Mitsugu Sato, Hitachinaka (JP); Naomasa Suzuki, Hitachinaka (JP)

(73) Assignee: Hitachi High Technologies Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/984,907

(22) Filed: Jan. 5, 2011

(65) Prior Publication Data

US 2011/0095184 A1    Apr. 28, 2011

Related U.S. Application Data

(63) Continuation of application No. 12/139,970, filed on Jun. 16, 2008, now Pat. No. 7,888,640.

(30) Foreign Application Priority Data

Jun. 18, 2007 (JP) ................................. 2007-160096

(51) Int. Cl.
*H01J 37/28* (2006.01)
*G01N 23/225* (2006.01)
(52) U.S. Cl. ....................................... 250/310; 250/307
(58) Field of Classification Search .................. 250/310, 250/307
See application file for complete search history.

(56) References Cited

U.S. PATENT DOCUMENTS

| 3,944,829 A * | 3/1976 | Sato .............................. 250/310 |
| 5,142,148 A | 8/1992 | Sato |
| 5,146,090 A | 9/1992 | Plies |
| 5,594,245 A | 1/1997 | Todokoro et al. |
| 5,874,735 A | 2/1999 | Matsumoto et al. |
| 6,583,413 B1 | 6/2003 | Shinada et al. |
| 7,888,640 B2 * | 2/2011 | Tachibana et al. ............ 250/310 |
| 2006/0226362 A1* | 10/2006 | Kitsuki et al. ................ 250/310 |

FOREIGN PATENT DOCUMENTS

JP         01-236563         9/1989

OTHER PUBLICATIONS

Entire Prosecution of U.S. Appl. No. 12/139,970 to Tachibana, et al., filed on Jun. 16, 2008, entitled "Scanning Electron Microscope and Method of Imaging an Object by Using the Scanning Electron Microscope".

* cited by examiner

*Primary Examiner* — Jack Berman
(74) *Attorney, Agent, or Firm* — McDermott Will & Emery LLP (57) ABSTRACT

A scanning electron microscope capable of modifying the focal position of a condenser lens with high speed and high reproducibility in order that low-magnification images are obtained at large depths of focus and that high-magnification images are obtained at high resolution. The microscope has a specimen-holding portion, an electron beam source, a condenser lens for converging the electron beam, an objective lens for focusing the converged beam into a very small spot onto a specimen, scan coils, a detector for detecting a specimen signal emanating from the specimen, and a display portion for displaying the detected specimen signal as an image. An axisymmetric electrode is disposed within the magnetic field produced by the condenser lens. A voltage is applied to the electrode.

8 Claims, 5 Drawing Sheets

SCANNING ELECTRON MICROSCOPE AND METHOD OF IMAGING AN OBJECT BY USING THE SCANNING ELECTRON MICROSCOPE

This application is a Continuation of U.S. patent application Ser. No. 12/139,970, filed on Jun. 16, 2008, now U.S. Pat. No. 7,888,640, claiming priority of Japanese Application No. 2007-160096, filed on Jun. 18, 2007, the disclosures of which Applications are incorporated by reference herein.

BACKGROUND OF THE INVENTION

The present invention relates to a scanning electron microscope for obtaining a two-dimensional image of a specimen by scanning a focused electron beam over the specimen and detecting the produced secondary signal. Especially, the invention relates to a scanning electron microscope for measuring patterns formed on substrates such as semiconductor substrates and for observing defects.

Semiconductor devices are fabricated by forming a pattern on a photomask, transferring the pattern onto a wafer by lithography and etching steps, and repeating this sequence of operations. In this manufacturing process, it is important to achieve a good yield quickly and to maintain stable operation of the production process. For these purposes, it is essential that in-line inspection of wafers be performed, found defects be quickly analyzed, causes of generation of the defects be sought for, and the sought causes be utilized for countermeasures. To quickly couple the results of inspection to a countermeasure for preventing defects, automatic defect review and classification technology for reviewing a number of detected defects at high speed and classifying them in terms of causes is a key technology. Furthermore, as the production process has become finer, defect sizes affecting the production yield of semiconductor devices have become finer. It is difficult to review defects at high resolution with an optical review tool. Therefore, defect-review SEMs (scanning electron microscopes) capable of reviewing defects at high speed and high resolution have been commercialized. In recent years, semiconductor devices have been fabricated at increasing scales of integration and with finer features. With these trends, various kinds of patterns have been formed on wafers. It has become more important to evaluate and measure the shapes and dimensions of the formed patterns. In order to measure a multiplicity of measurement points at high speed and stably, metrology SEMs capable of observing and measuring semiconductor patterns at high resolution have been commercialized.

The above-described scanning electron microscopes for inspection of semiconductor devices have a function of acquiring a high-magnification SEM image. In particular, a low-magnification SEM image of an object under observation is first derived. The low-magnification image has a large aperture angle. This image is searched for the object, and the object is brought to the center of the image. Then, the high-magnification SEM image is acquired for detailed observation.

The low-magnification image needs to have a large depth of focus to facilitate searching the image for the object. The high-magnification image needs high resolution to permit detailed observation. JP-A-1-236563 and US2006/0226362A1 (hereinafter referred to as patent references 1 and 2, respectively) describe techniques of obtaining large depths of focus by varying the excitation of the condenser lens to move the image point of the condenser lens and varying the aperture angle of the electron beam impinging on the specimen. Patent reference 1 does not mention of switching of the magnification. Patent reference 2 states that the aperture angle of the electron beam is varied according to the magnification such that a low-magnification image is obtained with a large depth of focus and that a high-magnification image is obtained with high resolution.

SUMMARY OF THE INVENTION

According to the descriptions of the above patent references JP-A-1-236563 and US2006/0226362A1, the excitation of an electromagnetic lens is varied as a means for moving the image point of the condenser lens. If the electrical current flowing through a coil is varied to vary the excitation of the electromagnetic lens, there is the possibility that the magnetic field is varied with delay by magnetic after-effect or the reproducibility is deteriorated by the effects of hysteresis.

Throughput is also a great factor for semiconductor inspection tools. Where the aperture angle of the electron beam is switched with an electromagnetic lens, a long time is taken to perform the switching operation. Consequently, there is the anxiety that the throughput is deteriorated.

It is a first object of the present invention to provide a technique for moving the focal point of a condenser lens at high speed in cases where the movement is made such that a low-magnification image is obtained with a large depth of focus and that a high-magnification image is obtained with high resolution.

It is a second object of the invention to provide a technique of enhancing the reproducibility of movement of the focal point of a condenser lens in cases where the movement is made such that a low-magnification image is obtained with a large depth of focus and that a high-magnification image is obtained with high resolution.

In the present invention, an axisymmetric electrode is mounted within the magnetic field produced by a condenser lens. A voltage is applied to the electrode to vary the energy of primary electrons passed through the magnetic field set up by the condenser lens. This moves the image point of the condenser lens, thus achieving the above-described objects.

That is, a scanning electron microscope according to the present invention has: a specimen-holding portion for holding a specimen; an electron beam source emitting an electron beam; a condenser lens for converging the electron beam emitted from the electron beam source; an objective lens for focusing the converged beam into a very small spot onto the specimen; scan coils for scanning the electron beam over the specimen; a detector for detecting a specimen signal emanating from the specimen in response to the electron beam irradiation; and a display portion for displaying the specimen signal detected by the detector as an image. An axisymmetric electrode is mounted within the magnetic field produced by the condenser lens. A voltage is applied to the electrode. Consequently, the image point of the condenser lens is moved with high speed and high reproducibility.

According to the present invention, movement of the image point of the condenser lens is made to obtain a low-magnification image with a large depth of focus and a high-magnification image is obtained with high resolution. This movement is achieved with high speed and high reproducibility.

Other objects, features and advantages of the invention will become apparent from the following description of the embodiments of the invention taken in conjunction with the accompanying drawings.

DETAILED DESCRIPTION OF THE EMBODIMENTS

Embodiments of the present invention are hereinafter described with reference to the drawings. In FIG. 2 and subsequent figures, those portions having the same functions as their counterparts of FIG. 1 are indicated by the same reference numerals as in FIG. 1 and their description is omitted.

Figure 1:
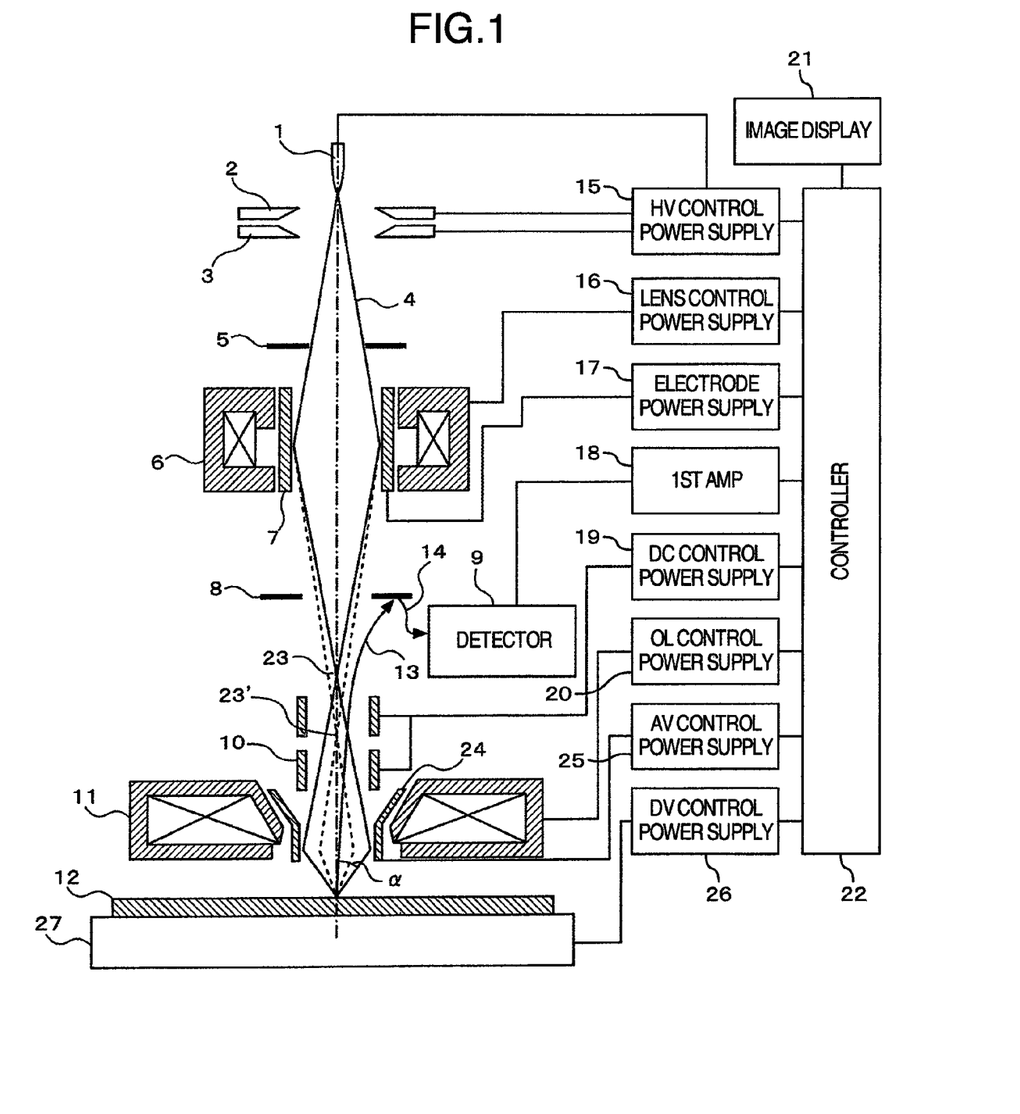
FIG. 1 is a vertical cross section showing the structure of a scanning electron microscope according to the present invention.
Figure 2:
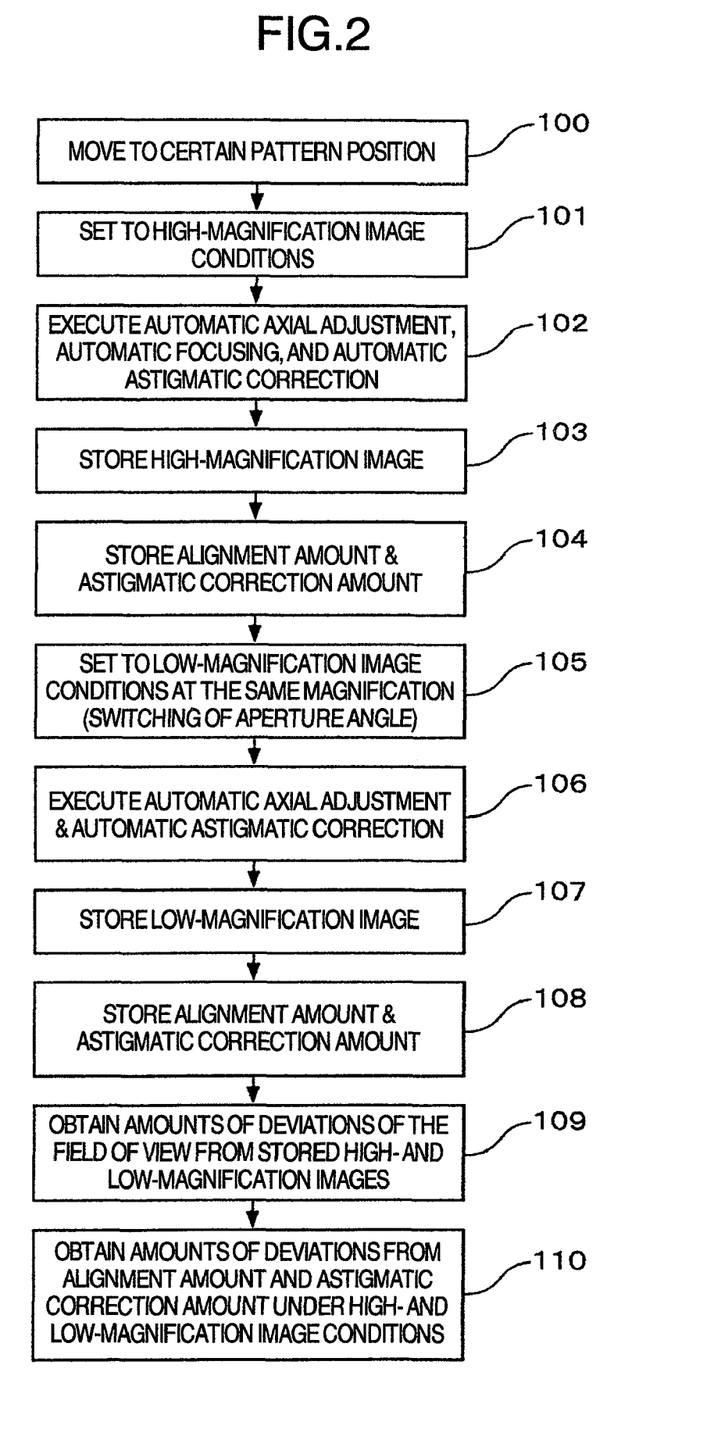
FIG. 2 is a flowchart illustrating a sequence of operations for automatically obtaining the amount of deviation produced by switching of an aperture angle.

FIG. 1 is a schematic cross-sectional view showing the structure of a scanning electron microscope according to a first embodiment of the present invention. In the figure, a vacuum vessel, a wafer-conveying system, and so on necessary for the scanning electron microscope are omitted. A voltage is applied between a cathode 1 and a first anode 2 from a high-voltage (HV) control power supply 15 that is under control of a controller 22. A given emission current is extracted from the cathode 1. An accelerating voltage is applied between the cathode 1 and a second anode 3 from the high-voltage control power supply 15 that is under control of the controller 22. Therefore, a primary electron beam 4 released from the cathode 1 is accelerated toward a rear stage of lenses. After undesired regions of the primary electron beam 4 are removed by an aperture plate 5, the beam 4 is focused at a focal position 23 by a condenser lens 6 that is under control of a lens control power supply 16.

Then, the primary electron beam 4 is focused into a very small spot onto a specimen 12 by an objective lens 11 that is under control of an objective lens (OL) control power supply 20. The beam is scanned in two dimensions over the specimen 12 by deflection coils 10 that are controlled by a deflection coil (DL) control power supply 19. A scan signal for the deflection coils 10 is controlled by the deflection coil control power supply 19 according to a final magnification. The scanning width of the primary electron beam 4 is determined by the final magnification. A positive voltage is applied to an acceleration electrode 24 disposed in the objective lens 11 by an accelerating voltage (AV) control power supply 25. A negative voltage is applied to the specimen 12 or to a specimen holder (not shown) holding the specimen 12 by a decelerating voltage control power supply. Consequently, the resolution is improved. The acceleration electrode 24 may be shared with the magnetic path of the objective lens 11.

The specimen 12 irradiated with the primary electron beam 4 produces a secondary signal 13 including secondary electrons and backscattered electrons. The secondary signal 13 travels to a region located over the objective lens 11, and then is collided against a conductive plate 8 having an aperture through which the primary electron beam 4 can be passed. Thus, secondary electrons 14 are produced. The secondary electrons 14 are detected by a detector 9. The output signal from the detector 9 is amplified by a first amplifier 18 and displayed as a specimen image on an image display device 21 in synchronism with the scan signal for the deflection coils 10.

In this case, the aperture angle α of the primary electron beam 4 is determined by the focal conditions for the condenser lens 6 and by the diameter of the aperture in the aperture plate 5. If the aperture angle α of the beam 4 is reduced, the depth of focus is increased but the resolution is deteriorated. Conversely, if the aperture angle α is increased, the depth of focus is reduced but the resolution is improved. However, if an optimum value of the aperture angle α is exceeded, the resolution is impaired by the effects of aberrations. An axisymmetric electrode 7 is disposed within the magnetic field produced by the condenser lens 6. If a voltage is applied to the electrode 7 from an electrode power supply 17, the energy of the primary electron beam 4 passed through the magnetic field produced by the condenser lens 6 is varied. This in turn varies the focal position 23 of the primary electron beam 4. In particular, if a positive voltage is applied to the electrode 7, the primary electron beam 4 passed through the condenser lens 6 is accelerated. As a result, the original focal position 23 shifts to a different focal position 23' on the side of the objective lens 11. Consequently, the aperture angle α of the primary electron beam 4 over the specimen 12 varies. This changes the depth of focus of the beam 4. Where a positive voltage is applied to the electrode 7, the aperture angle α decreases and so the depth of focus increases.

If a voltage is applied to the electrode 7 to move the focal position 23 of the condenser lens 6 into the different focal position 23', the beam on the specimen 12 will be out of focus provided that the excitation conditions of the objective lens 11 remain unchanged. Therefore, the beam must be focused by the objective lens 11. However, if the coil current in the objective lens 11 is varied to thereby modify the excitation conditions, it will be impossible to make focal settings with high speed and high reproducibility. Accordingly, the excitation of the objective lens 11 is not varied in order to focus the beam. The positive voltage applied to the acceleration electrode 24 is varied by the acceleration voltage control power supply 25. Thus, the beam on the specimen 12 is brought to a focus. At this time, an amount of variation to the voltage applied to the acceleration electrode 24 is calculated by a microprocessor (not shown) in the controller 22, based on the amount of variation from the focal position 23 to the different focal position 23'. Similar results can be obtained if the negative voltage applied to the specimen 12 from a deceleration voltage (DV) control power supply 26 is varied. The positive voltage applied to the acceleration electrode 24 or the negative voltage applied to the specimen 12 is varied simultaneously with the application of the voltage to the electrode 7. Consequently, the aperture angle α can be modified with high speed and high reproducibility.

The above-described technique is used as follows in a scanning electron microscope for inspection of semiconductor devices. When a low-magnification image is obtained at a low final magnification (i.e., at a wide aperture angle achieved by increasing the scanning width of the primary electron beam 4), the operating conditions are so set that a large depth of focus can be achieved such that the object to be observed can be easily searched for without the need to focus the beam. When a high-magnification image is obtained at a high final magnification by reducing both scanning width of the primary electron beam 4 and aperture angle for detailed observation, the operating conditions achieving high resolution are so adjusted that the aperture angle α is switched. Where emphasis is placed on the throughput, it is necessary to switch the magnification of the image between low magnification and high magnification with high speed and high reproducibility. According to the present invention, its effect can be produced sufficiently.

If the aperture angle α is switched when the magnification of the image is switched from low to high value or vice versa, there is the possibility that a deviation of the field of view, a misalignment, and a deviation of the amount of astigmatic correction take place. With respect to a deviation of the field of view, the amount of deviation of the field of view occurring when the aperture angle α is switched can be corrected using an electrical coil for moving the field of view. This electrical coil is not shown but is already known as an image shift coil, as described in U.S. Pat. No. 5,874,735. Furthermore, a misalignment can be corrected by storing either an amount of alignment obtained by an alignment coil (not shown) that performs an alignment through the center of the objective lens 11 or its amount of misalignment into the controller 22 and using the stored value when the aperture angle α is switched. A deviation of the amount of astigmatic correction can be corrected by storing an amount of correction to the astigmatic coil (not shown) into the controller 22 and setting the amount, in the same way as a misalignment.

Previously stored values can be used as these amounts of corrections to the deviations. Alternatively, measurements may be made prior to observation and stored in memory. In the case of a scanning electron microscope for semiconductor inspection, it is required to automate measurements of amounts of corrections to deviations prior to observation. In order to obtain the amounts of corrections, a sequence of operations as shown in FIG. 2 may be carried out.

FIG. 2 is a flowchart illustrating the sequence of operations for automatically obtaining an amount of deviation produced when the aperture angle is switched. First, movement to a certain pattern position is made (step 100). Specifically, a dedicated pattern is previously prepared on a stage mechanism 27 to permit automatic axial adjustment, automatic focusing, and automatic astigmatic correction to be carried out in later process steps accurately, and the pattern is used. Then, operating conditions under which the aperture angle α gives rise to a high resolution for obtaining a high-magnification image are set (step 101). The automatic axial adjustment, automatic focusing, and automatic astigmatic correction are carried out (step 102). The high-magnification image is stored in the memory of the controller 22 (step 103). The amount of alignment and amount of astigmatic correction are stored in the memory of the controller 22 (step 104). A voltage is applied to the electrode 7 under the conditions of the aperture angle α where the depth of focus is set large for acquisition of a low-magnification image without moving the specimen 12 at the same magnification. The aperture angle α is switched by modifying either the voltage applied to the acceleration electrode 24 or the voltage applied to the specimen 12 (step 105). The magnification at which the aperture angle α is switched may be modified if an amount of deviation of the field of view can be normally obtained in a later step.

After the switching of the aperture angle α, the automatic axial adjustment and automatic astigmatic correction are carried out (step 106). The image is stored in the memory of the controller 22 (step 107). The amount of alignment and amount of astigmatic correction are stored in the memory of the controller 22 (step 108). The amount of movement of the field of view made when the aperture angle α was switched is obtained from the images stored in steps 103 and 107 (step 109) and stored in the memory of the controller 22. An amount of deviation of the amount of alignment and an amount of deviation of the amount of astigmatic correction are obtained from the amounts of alignment and amounts of astigmatic correction derived before and after the switching of the aperture angle α, the latter amounts being stored in steps 104 and 108 (step 110). The amounts of deviations are stored in the memory of the controller 22. By performing the steps described so far, the amount of deviation of the field of view caused by the switching of the aperture angle α can be automatically obtained.

Figure 3:
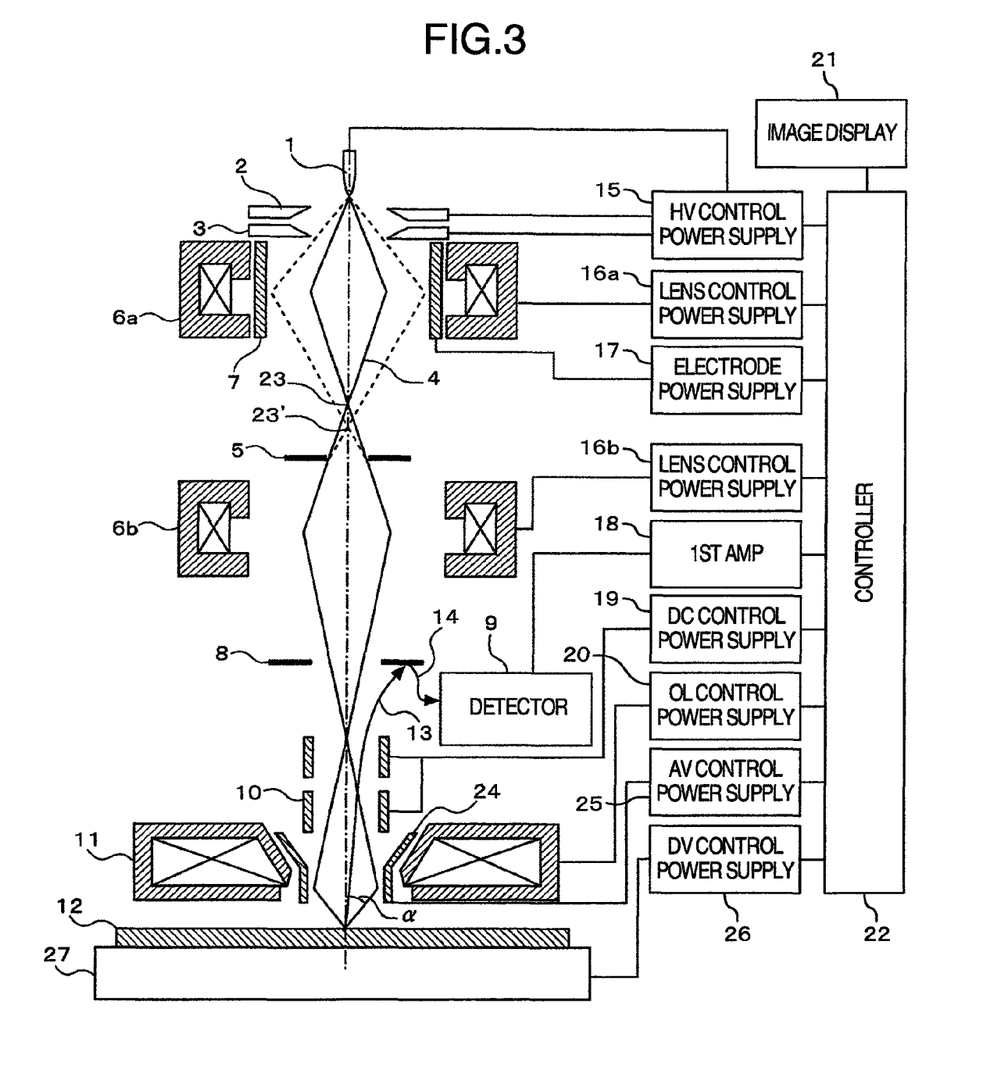
FIG. 3 is a vertical cross section showing the structure of another scanning electron microscope according to the invention.

FIG. 3 is a vertical cross section showing the structure of a scanning electron microscope according to a second embodiment of the present invention. This structure is similar to the structure already described in connection with FIG. 1 except that the condenser lens 6 of FIG. 1 is replaced by two stages of condenser lenses consisting of a first condenser lens 6a and a second condenser lens 6b that are controlled by lens control power supplies 16a and 16b, respectively. The aperture plate 5 is disposed between the first condenser lens 6a and the second condenser lens 6b to remove regions not necessary for formation of an image from the primary electron beam 4. Then, the beam is converged by the second condenser lens 6b and focused into a very small spot onto the specimen 12 by the objective lens 11 that is under control of the objective lens control power supply 20. The amount of the primary electron beam 4 passed through the aperture plate 5 is adjusted by controlling the focal position 23 of the first condenser lens 6a. Consequently, the amount of the primary electron beam 4 impinging on the specimen 12 can be controlled. Moreover, the aperture angle α of the beam 4 can be controlled by controlling the focal position of the second condenser lens 6b.

The axisymmetric electrode 7 is disposed within the magnetic field developed by the first condenser lens 6a. When a voltage is applied to the electrode 7, the energy of the primary electron beam 4 passed through the field produced by the first lens 6a is varied. This varies the focal position 23 of the electron beam 4. In particular, if a positive voltage is applied to the electrode 7, the primary electron beam 4 passed through the first condenser lens 6a is accelerated. This shifts the focal position from the original position 23 to the focal position 23' on the side of the aperture plate 5. Therefore, the amount of the beam 4 passed through the aperture plate 5 increases, thus increasing the amount of the primary electron beam 4 impinging on the specimen 12. The amount of the primary electron beam 4 impinging on the specimen 12 can be varied with high speed and high reproducibility by applying the voltage to the electrode 7.

Figure 4:
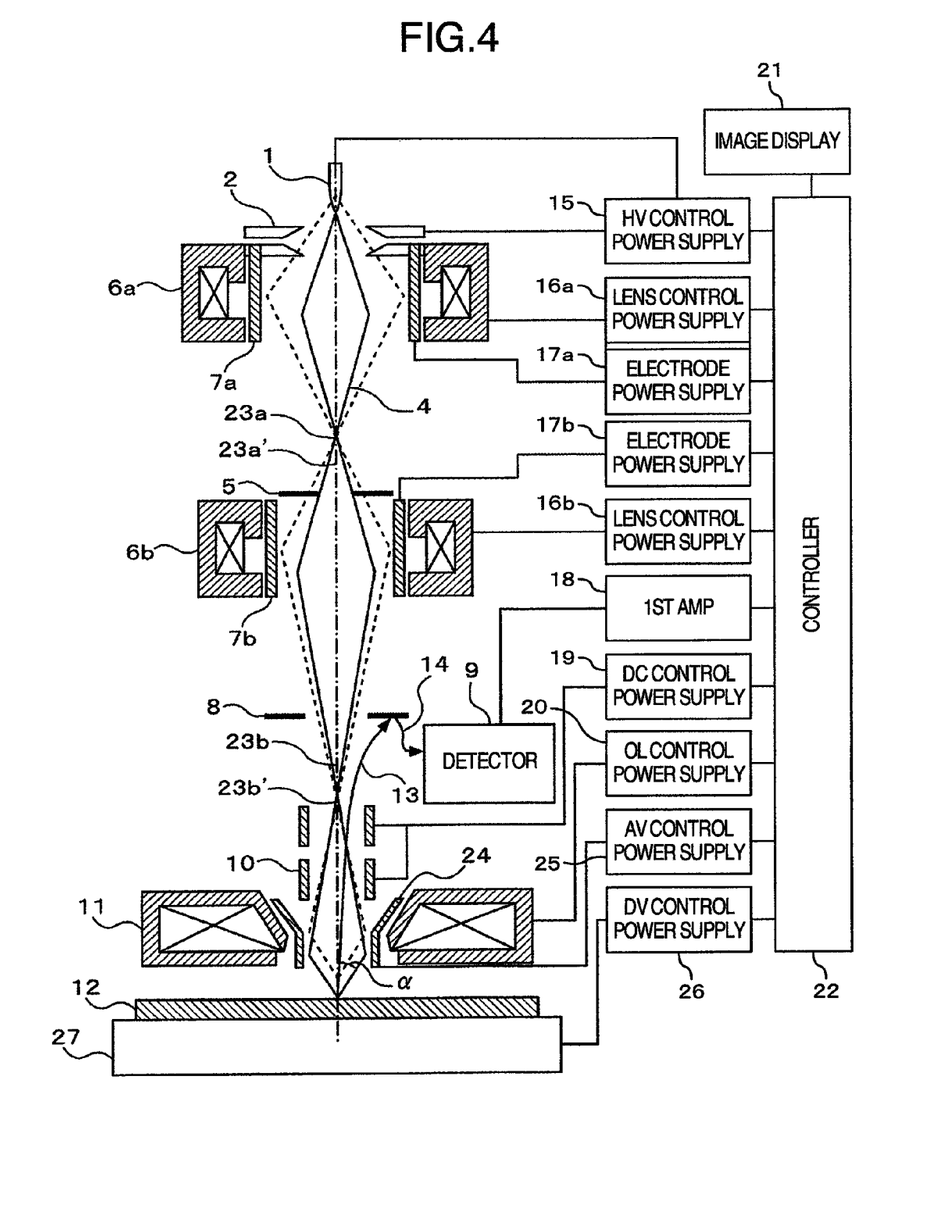
FIG. 4 is a vertical cross section showing the structure of a further scanning electron microscope according to the invention.

FIG. 4 is a vertical cross section showing the structure of a scanning electron microscope according to a third embodiment of the present invention. This structure is characterized in that an axisymmetric electrode 7b is disposed within the magnetic field generated by the second condenser lens 6b shown in FIG. 3. The aperture angle α is determined by the focal position 23a of the first condenser lens 6a, the diameter of the aperture in the aperture plate 5, and the focal position 23b of the second condenser lens. When a voltage is applied to the axisymmetric electrode 7a disposed within the magnetic field set up by the first condenser lens 6a from an electrode power supply 17b, the focal position 23a of the first condenser lens 6a varies, thus changing the amount of the primary electron beam 4 impinging on the specimen 12. However, the aperture angle α also varies because the focal position 23a of the first condenser lens 6a varies. Accordingly, the aperture angle α can be controlled by applying a voltage to the axisymmetric electrode 7b disposed within the magnetic field produced by the second condenser lens 6b from an electrode power supply 17b.

At the same time, the beam is brought to a focus by controlling either the voltage applied to the acceleration electrode 24 or the voltage applied to the specimen 12 without varying the excitation conditions of the objective lens 11. An amount by which the voltage to the electrode 7a is varied is computed from an amount by which the irradiation should be varied. An amount by which the voltage to the electrode 7b is varied is calculated from a desired amount by which the aperture angle α is varied. Furthermore, either the voltage applied to the acceleration electrode 24 or the voltage applied to the specimen 12 is calculated to focus the beam onto the specimen. The amount of the primary electron beam 4 impinging on the specimen and the aperture angle α can be simultaneously modified with high speed and high reproducibility by controlling these three voltages.

Figure 5:
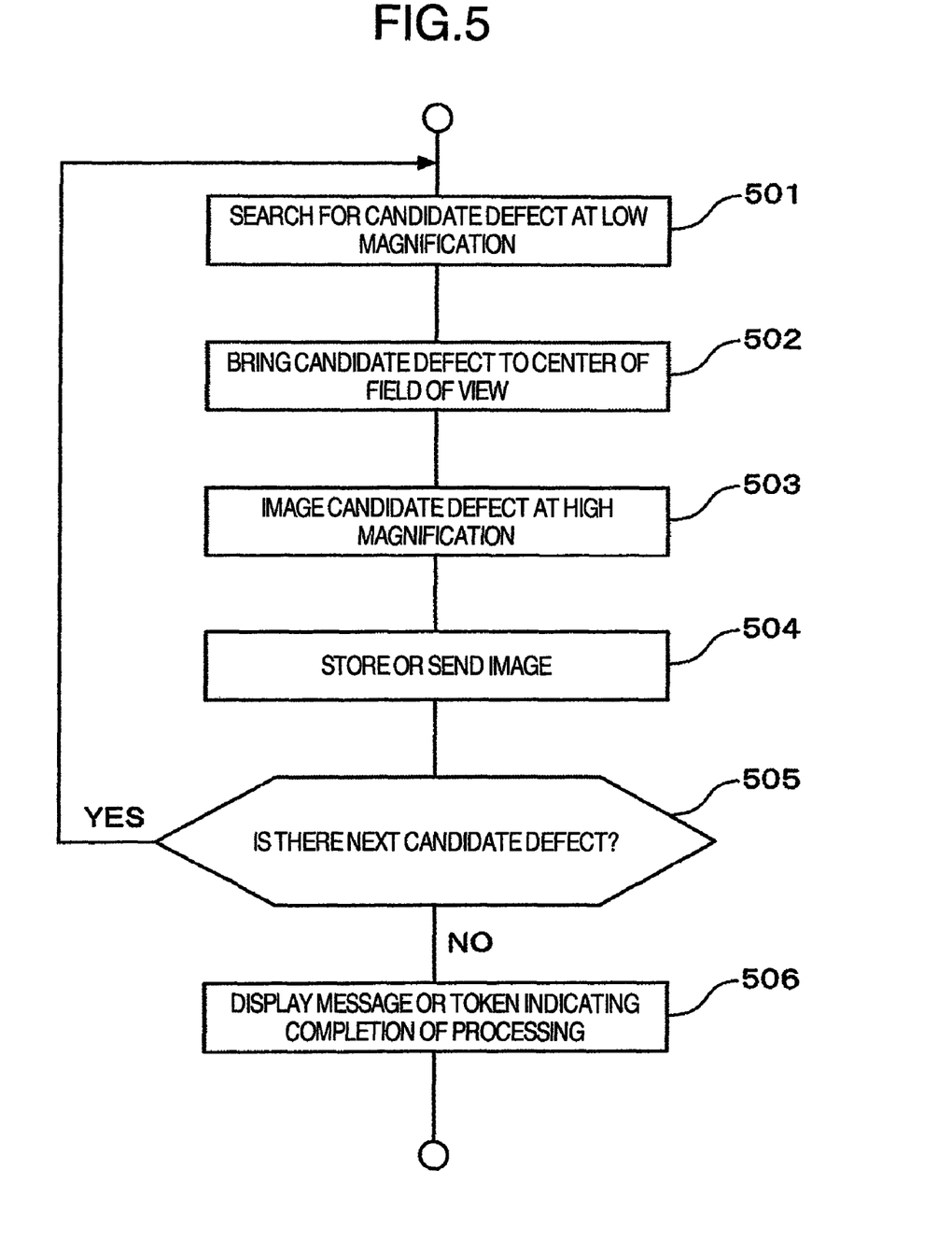
FIG. 5 is a flowchart illustrating a procedure for searching for a candidate defect.

Foreign matter on a substrate (such as a semiconductor substrate) is observed or defects of the formed pattern are observed, using a review SEM, based on the principle described so far. FIG. 5 is a flowchart illustrating a procedure for searching for a candidate defect. Foreign matter or a defect is detected by an optical inspection system or an electron beam inspection system utilizing an electron microscope. The coordinates of the detected foreign matter or defect are sent out. The detected defect is not yet analyzed closely. It is not yet known as to whether it is a true defect. Therefore, it is herein referred to as a candidate defect. The substrate is conveyed to the review SEM from the aforementioned inspection system. An image for observation is taken under preset electron optical conditions. In the review SEM, the magnification at which the image is taken for analysis of the candidate defect is set based on information about the size of the candidate defect such that the size is contained within the field of view of the image. The magnification at which a candidate defect is searched for is set such that the size of the candidate defect is larger than the size of each pixel of the image and covers a wide area which permits the candidate defect to be found easily.

First, a candidate defect is searched for at a low magnification, based on the coordinates of the candidate defect sent from the inspection system, and then the defect is detected (step 501). If the candidate defect is detected, the candidate defect is brought closest to the center of the field of view of the image by moving the substrate or adjusting the range of deflection scanned by the primary electron beam (step 502). Then, the scanning width of the primary electron beam is reduced and higher-magnification image is taken (step 503). Then, the image is stored or sent to a storage device mounted separately (step 504). If there is a next candidate defect (step 505), the magnification is switched back to a lower value. The process returns to step 501, where a next candidate defect is searched for. These steps are repeated. When imaging of the defect candidate is completed, a message or token indicating completion of the processing is displayed on the display unit (step 506).

The aforementioned method of the present invention is used when the magnification is switched from a low value to a high value or vice versa. Consequently, a large depth of focus is obtained at a low magnification. This makes it easy to search for a candidate defect. At high magnification, a high-resolution image can be derived. Furthermore, the magnification can be switched accurately and at high speed.

In addition, the present invention has the following configurations:

(1) A scanning electron microscope comprising:
  a first condenser lens for converging an electron beam emitted from an electron beam source;
  an electrode having an axisymmetric shape and disposed in a magnetic field produced by the first condenser lens;
  a second condenser lens for converging the electron beam which has been passed through the first condenser lens after being emitted from the electron beam source;
  an aperture plate disposed in a region containing an optical axis between the first and second condenser lenses;
  an objective lens for focusing the converged electron beam into a very small spot onto a specimen;
  scan coils for scanning the electron beam over the specimen;
  a detector for detecting a specimen signal emanating from the specimen in response to the electron beam irradiation;
  an acceleration electrode mounted in the objective lens and acting to accelerate a primary electron beam reaching from the electron beam source; and
  a control unit for controlling an amount of the primary electron beam passed through the aperture plate by applying a given voltage to the electrode.

(2) A scanning electron microscope comprising:
  a first condenser lens for converging an electron beam emitted from an electron beam source;
  a first electrode having an axisymmetric shape and disposed in a magnetic field produced by the first condenser lens;
  a second condenser lens for converging the electron beam which has been passed through the first condenser lens after being emitted from the electron beam source;
  a second electrode having an axisymmetric shape and disposed in a magnetic field produced by the second condenser lens;
  an aperture plate disposed in a region containing an optical axis between the first and second condenser lenses;
  an objective lens for focusing the converged electron beam into a very small spot onto a specimen;
  scan coils for scanning the electron beam over the specimen;
  a detector for detecting a specimen signal emanating from the specimen in response to the electron beam irradiation;
  an acceleration electrode mounted in the objective lens and acting to accelerate a primary electron beam reaching from the electron beam source; and
  a control unit for controlling an amount of the primary electron beam passed through the aperture plate by applying a given voltage to an electrode mounted within the first condenser lens, the control unit acting also to vary a focal position of the second condenser lens without modifying the focus of the objective lens by varying the voltage applied to the acceleration electrode while applying the given voltage to an electrode mounted within the second condenser lens.

(3) A scanning electron microscope comprising:
  a first condenser lens for converging an electron beam emitted from an electron beam source;
  a first electrode having an axisymmetric shape and disposed in a magnetic field produced by the first condenser lens;
  a second condenser lens for converging the electron beam which has been passed through the first condenser lens after being emitted from the electron beam source;
  a second electrode having an axisymmetric shape and disposed in a magnetic field produced by the second condenser lens;
  an aperture plate disposed in a region containing an optical axis between the first and second condenser lenses;
  an objective lens for focusing the converged electron beam into a very small spot onto a specimen;
  scan coils for scanning the electron beam over the specimen;
  a detector for detecting a specimen signal emanating from the specimen in response to the electron beam irradiation;

means for applying a negative voltage to the specimen or to a specimen-holding portion that holds the specimen to decelerate the primary electron beam; and
a control unit for controlling an amount of the primary electron beam passed through the aperture plate by applying a given voltage to an electrode mounted within the first condenser lens, the control unit acting also to vary a focal position of the second condenser lens without modifying the focus of the objective lens by varying the negative voltage applied to the specimen-holding portion while applying the given voltage to an electrode mounted within the second condenser lens.

(4) The scanning electron microscope of (2) above, further comprising:
a display portion for causing the specimen signal detected by the detector to be displayed as an image.

(5) A scanning electron microscope for creating an image of a specimen by irradiating the specimen with an electron beam and detecting a signal emanating from the specimen, the scanning electron microscope comprising:
a condenser lens for converging the electron beam such that the electron beam is sharply focused over the specimen;
a deflector for scanning the sharply focused electron beam over the specimen;
a scanning width control unit for modifying a scanning width of the electron beam scanned by the deflector;
an electrode for modifying an aperture angle of the focused electron beam; and
a control unit for causing the electrode to modify the aperture angle of the electron beam when the scanning width of the beam is modified by the scanning width control unit.

(6) The scanning electron microscope of (5) above, wherein the control unit modifies the aperture angle to a larger value when the scanning width is modified to a smaller value.

(7) The scanning electron microscope of (5) above, wherein the control unit modifies the aperture angle to a smaller value when the scanning width is modified to a larger value.

(8) A scanning electron microscope for creating an image of a specimen by irradiating the specimen with an electron beam and detecting a signal emanating from the specimen, the scanning electron microscope comprising:
an input device for entering irradiation conditions under which the specimen is irradiated with the electron beam;
a storage device for storing the entered conditions;
a control unit for reading out the conditions stored in the storage device and causing the specimen to be irradiated with the electron beam under the conditions read out; and
a display device for displaying the conditions stored in the storage device;
wherein the input device permits at least two scanning widths of the electron beam scanned over the specimen to be entered; and
wherein the control unit selects condition items corresponding to said at least two scanning widths from the conditions stored in the storage device and repeats the irradiation of the specimen with the electron beam.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A scanning electron microscope comprising:
a first condenser lens for converging an electron beam emitted from an electron beam source;
an electrode having an axisymmetric shape and disposed in a magnetic field produced by the first condenser lens;
a second condenser lens for converging the electron beam which has been passed through the first condenser lens after being emitted from the electron beam source;
an aperture plate disposed in a region containing an optical axis between the first and second condenser lenses;
an objective lens for focusing the converged electron beam into a very small spot onto a specimen;
scan coils for scanning the electron beam over the specimen;
a detector for detecting a specimen signal emanating from the specimen in response to the electron beam irradiation;
an acceleration electrode mounted in the objective lens and acting to accelerate a primary electron beam reaching from the electron beam source; and
a control unit for controlling an amount of the primary electron beam passed through the aperture plate by applying a given voltage to the electrode.

2. A scanning electron microscope comprising:
a first condenser lens for converging an electron beam emitted from an electron beam source;
a first electrode having an axisymmetric shape and disposed in a magnetic field produced by the first condenser lens;
a second condenser lens for converging the electron beam which has been passed through the first condenser lens after being emitted from the electron beam source;
a second electrode having an axisymmetric shape and disposed in a magnetic field produced by the second condenser lens;
an aperture plate disposed in a region containing an optical axis between the first and second condenser lenses;
an objective lens for focusing the converged electron beam into a very small spot onto a specimen;
scan coils for scanning the electron beam over the specimen;
a detector for detecting a specimen signal emanating from the specimen in response to the electron beam irradiation;
an acceleration electrode mounted in the objective lens and acting to accelerate a primary electron beam reaching from the electron beam source; and
a control unit for controlling an amount of the primary electron beam passed through the aperture plate by applying a given voltage to an electrode mounted within the first condenser lens, the control unit acting also to vary a focal position of the second condenser lens without modifying the focus of the objective lens by varying the voltage applied to the acceleration electrode while applying the given voltage to an electrode mounted within the second condenser lens.

3. A scanning electron microscope comprising:
a first condenser lens for converging an electron beam emitted from an electron beam source;
a first electrode having an axisymmetric shape and disposed in a magnetic field produced by the first condenser lens;
a second condenser lens for converging the electron beam which has been passed through the first condenser lens after being emitted from the electron beam source;

a second electrode having an axisymmetric shape and disposed in a magnetic field produced by the second condenser lens;

an aperture plate disposed in a region containing an optical axis between the first and second condenser lenses;

an objective lens for focusing the converged electron beam into a very small spot onto a specimen;

scan coils for scanning the electron beam over the specimen;

a detector for detecting a specimen signal emanating from the specimen in response to the electron beam irradiation;

means for applying a negative voltage to the specimen or to a specimen-holding portion that holds the specimen to decelerate the primary electron beam; and a control unit for controlling an amount of the primary electron beam passed through the aperture plate by applying a given voltage to an electrode mounted within the first condenser lens, the control unit acting also to vary a focal position of the second condenser lens without modifying the focus of the objective lens by varying the negative voltage applied to the specimen-holding portion while applying the given voltage to an electrode mounted within the second condenser lens.

4. The scanning electron microscope of claim 2, further comprising:

a display portion for causing the specimen signal detected by the detector to be displayed as an image.

5. A scanning electron microscope for creating an image of a specimen by irradiating the specimen with an electron beam and detecting a signal emanating from the specimen, the scanning electron microscope comprising:

a condenser lens for converging the electron beam such that the electron beam is sharply focused over the specimen;

a deflector for scanning the sharply focused electron beam over the specimen;

a scanning width control unit for modifying a scanning width of the electron beam scanned by the deflector;

an electrode for modifying an aperture angle of the focused electron beam; and a control unit for causing the electrode to modify the aperture angle of the electron beam when the scanning width of the beam is modified by the scanning width control unit.

6. The scanning electron microscope of claim 5, wherein the control unit modifies the aperture angle to a larger value when the scanning width is modified to a smaller value.

7. The scanning electron microscope of claim 5, wherein the control unit modifies the aperture angle to a smaller value when the scanning width is modified to a larger value.

8. The scanning electron microscope of claim 5, further comprising:

an input device for permitting at least two scanning widths of the electron beam scanned over the specimen to be entered;

a storage device for storing the entered scanning widths; and a display device for displaying the scanning widths stored in the storage device, wherein the control unit selects condition items corresponding to said at least two scanning widths from the scanning widths stored in the storage device.

* * * * *